US009492652B2

(12) United States Patent
Moss et al.

(10) Patent No.: US 9,492,652 B2
(45) Date of Patent: Nov. 15, 2016

(54) IMPLANTABLE DEVICES THAT GENERATE LOW INTENSITY ELECTRIC FIELDS FOR THE TREATMENT OF ATHEROSCLEROTIC DISEASE AND PREVENTION OF ISCHEMIC VASCULAR EVENTS AND METHODS OF MANUFACTURE

(75) Inventors: Arthur Jay Moss, Rochester, NY (US); Ilan Goldenberg, Givat Shmuel (IL)

(73) Assignee: University of Rochester, Rochester, NY (US)

( * ) Notice: Subject to any disclaimer, the term of this patent is extended or adjusted under 35 U.S.C. 154(b) by 114 days.

(21) Appl. No.: 13/581,313

(22) PCT Filed: Mar. 1, 2011

(86) PCT No.: PCT/US2011/026760
§ 371 (c)(1),
(2), (4) Date: Sep. 20, 2012

(87) PCT Pub. No.: WO2011/109447
PCT Pub. Date: Sep. 9, 2011

(65) Prior Publication Data
US 2013/0190848 A1    Jul. 25, 2013

Related U.S. Application Data

(60) Provisional application No. 61/309,613, filed on Mar. 2, 2010.

(51) Int. Cl.
*A61N 1/05* (2006.01)
*A61F 2/24* (2006.01)
*A61F 2/07* (2013.01)
*A61N 1/20* (2006.01)
(Continued)

(52) U.S. Cl.
CPC . *A61N 1/05* (2013.01); *A61F 2/07* (2013.01); *A61F 2/2418* (2013.01); *A61N 1/205* (2013.01); *A61F 2/82* (2013.01); *A61N 1/378* (2013.01)

(58) Field of Classification Search
CPC ........... A61F 2/82; A61F 2/07; A61F 2/2418
USPC ........................................... 607/121
See application file for complete search history.

(56) References Cited

U.S. PATENT DOCUMENTS 3,723,754 A * 3/1973 Murayama et al. .......... 307/400
4,291,245 A * 9/1981 Nowlin et al. ............... 307/400
5,019,393 A * 5/1991 Ito et al. ...................... 424/423

(Continued)

FOREIGN PATENT DOCUMENTS

WO    WO 2012/177156 A1    12/2012

OTHER PUBLICATIONS

PCT International Search Report and Written Opinion for International Application No. PCT/US2011/026760; Date of Mailing Aug. 8, 2011. 12 pages.

*Primary Examiner* — Christopher D Koharski
*Assistant Examiner* — Jeremiah Kimball
(74) *Attorney, Agent, or Firm* — Patent Technologies, LLC; Robert D. Gunderman, Jr.

(57) ABSTRACT

An internal medical device for implantation into a human or animal where the internal medical device has an electric field source that may be an active source of electromotive force such as a battery or capacitor, or may be an electric field generating material such as an electret, piezoelectric, or the like.

7 Claims, 6 Drawing Sheets

(51) Int. Cl.
*A61N 1/378* (2006.01)
*A61F 2/82* (2013.01)

(56) References Cited

U.S. PATENT DOCUMENTS

| | | | |
|---|---|---|---|
| 5,603,731 A | 2/1997 | Whitney | |
| 6,585,763 B1* | 7/2003 | Keilman et al. | 623/1.42 |
| 6,673,104 B2 | 1/2004 | Barry | |
| 7,738,953 B2 | 6/2010 | Zhu et al. | |
| 7,850,645 B2 | 12/2010 | Atanasoska et al. | |
| 7,873,417 B2 | 1/2011 | Demarais et al. | |
| 8,530,004 B2* | 9/2013 | Huang et al. | 427/533 |
| 2002/0169480 A1* | 11/2002 | Zhu et al. | 607/2 |
| 2004/0073295 A1* | 4/2004 | Chaikof et al. | 623/1.46 |
| 2004/0094873 A1* | 5/2004 | Dubson et al. | 264/465 |
| 2004/0115831 A1* | 6/2004 | Meathrel et al. | 436/514 |
| 2004/0181278 A1* | 9/2004 | Tseng | A61F 2/07 623/1.46 |
| 2006/0034769 A1* | 2/2006 | Kohn | A61L 31/06 424/9.45 |
| 2006/0106451 A1 | 5/2006 | Busiashvili | |
| 2007/0129746 A1* | 6/2007 | Mische | 606/191 |
| 2007/0225800 A1* | 9/2007 | Sahatjian et al. | 623/1.42 |
| 2008/0208315 A1* | 8/2008 | Yang et al. | 623/1.15 |
| 2009/0036975 A1* | 2/2009 | Ward et al. | 623/1.18 |
| 2010/0076517 A1* | 3/2010 | Imran | 607/35 |
| 2010/0160756 A1* | 6/2010 | Petisce et al. | 600/345 |
| 2012/0213838 A1* | 8/2012 | Egashira | A61F 2/82 424/423 |

* cited by examiner

IMPLANTABLE DEVICES THAT GENERATE LOW INTENSITY ELECTRIC FIELDS FOR THE TREATMENT OF ATHEROSCLEROTIC DISEASE AND PREVENTION OF ISCHEMIC VASCULAR EVENTS AND METHODS OF MANUFACTURE

This application claims priority to U.S. patent application Ser. No. 61/309,613 filed Mar. 2, 2010 entitled "Implantable Devices That Generate Low Intensity Electrical. Fields For the Treatment of Atherosclerotic Disease And Prevention Of Ischemic Vascular Events And Methods of Use" and to International Application Number PCT/US11/26760 filed Mar. 1, 2011 entitled "Implantable Devices That Generate Low Intensity Electric Fields For the Treatment of Atherosclerotic Disease And Prevention Of Ischemic Vascular Events And Methods of Manufacture", the entire disclosures of which are incorporated herein, by reference.

BACKGROUND OF THE INVENTION

1. Field of the Invention

The present invention relates to devices and methods for applying electric fields to treat atherosclerotic disease. The present invention also relates to devices and methods adapted for prevention of ischemic vascular events.

2. Description of the Related Art

Implantable medical devices such as stents, vascular grafts, cardiac rhythm management devices, catheters, vena cava filters, and the like, are well known. Over the years, numerous improvements to these devices have occurred. There are still, however, difficulties. For example, in-stent restenosis is a complication where there is a reclosure of a previously stenosed coronary artery. Atherosclerosis, a common disease of the arteries, occurs where fatty material accumulates on the smooth muscle of a vessel wall, resulting in the eventual impediment of blood flow. Cardiac rhythm management devices such as pacemakers and implantable cardioverter defibrillators at times require the removal and replacement of an implanted endocardial lead. This need may arise for a variety of reasons, such as growth (in the case of children), lead failures, infections, and the like. The ease of lead removal and associated risk varies with the time that the implanted endocardial lead has been in place. A t lead that has been in place for three months or less is usually easily removed. However, a lead that has been in place for a year or longer presents removal difficulties due to fibrosis and encapsulation. These difficulties are in turn associated with mortality and significant morbidity. Pacing lead removal using simple traction is straightforward and with few complications. Unfortunately, fibrous adhesions to the Lead body complicate lead extraction and require more complex extraction techniques such as invasive surgical techniques and the use of assistive tools. As contemporary leads in use today are low profile and primarily coaxial bipolar, they do not stand up to simple traction where there is significant fibrosis present and the Lead is chronically implanted as a result. Polymethane insulated pacing leads see less fibrosis than the earlier silastic leads, but chronically implanted leads are still common. What is needed is a device that prevents fibrosis in medical devices such as cardiac pacing device leads. It is therefore an object of the present invention to provide an internal medical device that prevents or reduces fibrosis. It is another object of the present invention to provide an internal medical device that prevents or reduces fibrosis without the need for an external power source. It is another object of the present invention to provide an internal medical device that reduces atherosclerotic disease and ischemic vascular events. It is yet another object of the present invention to provide a stent for transluminal implantation that reduces the occurrence of in-stent restenosis. It is another object of the present invention to provide a vascular graft with improved healing characteristics.

BRIEF SUMMARY OF THE INVENTION

In accordance with the present invention, there is provided a medical device comprising an electric field source. The electric field source may be an electric field generating material or structure. A process for making an antithrombotic coating for a medical device where the coating comprises an electric field generating material or structure is further disclosed.

The foregoing paragraph has been provided by way of introduction, and is not intended to limit the scope of the following claims.

BRIEF DESCRIPTION OF THE DRAWINGS

The invention will be described by reference to the following drawings, in which like numerals refer to like elements, and in which.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as defined by this specification, drawings, and the appended claims.

DESCRIPTION OF THE PREFERRED EMBODIMENTS

Electrical stimulation using low intensity electric fields has been shown to protect the vascular wall through endothelial dependent (increased nitric oxide production) and independent mechanisms. In addition, low intensity electric field stimulation can lead to enhanced angiogenesis through increased expression of the Vascular Endothelial Growth Factor (VEGF) protein gene. This protection can be applied to various medical devices such as stents, vascular grafts, cardiac rhythm management devices, catheters, vena cava filters, and the like. The therapeutic effects of an applied electric field or charge distribution on these various medical devices includes, for example, reduced incidence of in-stent restenosis, reduced occlusion of prosthetic vascular grafts and similar devices, decreased incidence of fibrosis and encapsulation around a lead such as an endocardial lead in a cardiac rhythm management device, and the like. Without wishing to be bound to any particular theory, applicants believe that a charge distribution such as a negative charge distribution and associated electric field that is placed about an internal medical device repels platelets, which are known to have a negative charge, and in doing so inhibit clotting.

The benefits associated with the invention and the various embodiments described and envisioned herein were validated by a study of 1232 patients enrolled in a Multicenter Automatic Defibrillator Trial II (MADIT II). The patients were randomly assigned to either Implantable Cardioverter Defibrillator ("ICD") or non-ICD therapy and followed for a mean period of two years. The analysis of the MADIT II data confirmed that implantable devices according to the present invention are associated with a substantial reduction in the progression of coronary artery disease among patients who had stable angina at the onset of the trial.

Figure 1:
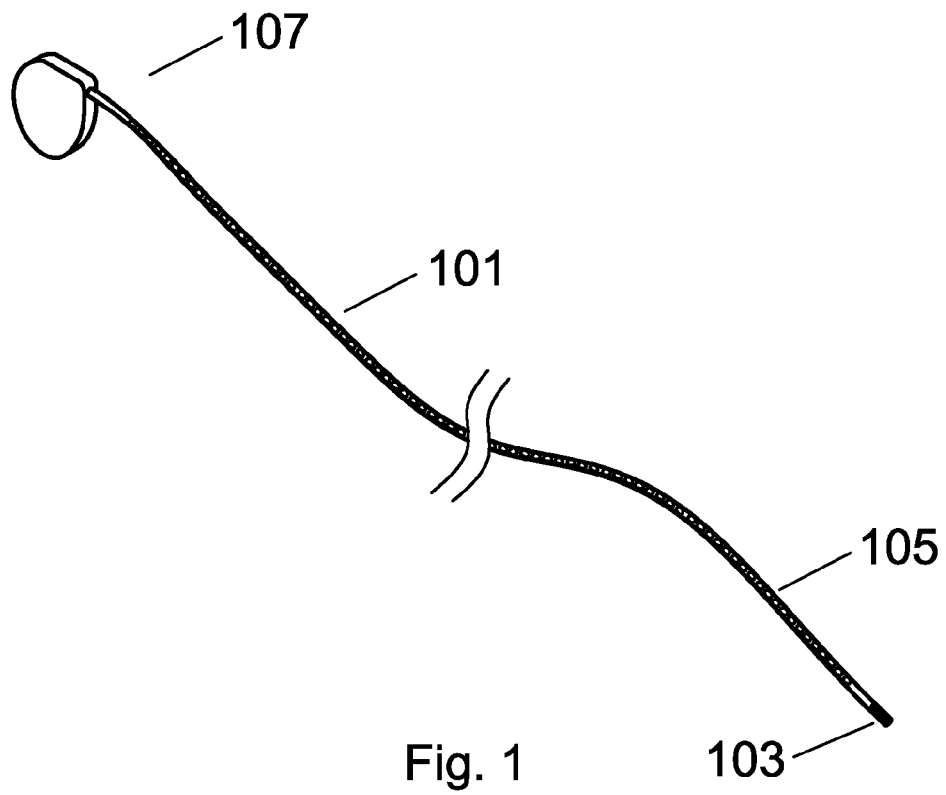
FIG. 1 depicts a cardiac rhythm management device having a lead with an electric field with an electric field source.

FIG. 1 depicts a cardiac rhythm management device having a lead with an electric field with an electric field source. The cardiac rhythm management device comprises a medical device 107 and an elongated main body lead 101. The medical device 107 comprises electronics that perform cardiac rhythm management functions that are electrically delivered to the heart by way of implantation of a metal tip 103 within a region of the myocardium. In one embodiment of the present invention, a coil or similar electrode structure 105 is contained along at least a section of the length of the elongated main body lead 101. The medical device 107 contains a battery, capacitor, or other electrical charge storage device that is electrically connected to the metal tip 103 and the coil or similar electrode structure 105. In some embodiments of the present invention, electrodes that are integral to the lead 101 for cardiac rhythm management functionality may be used to further create a low level electric field for therapeutic purposes including, but not limited to, the reduction of fibrosis along the length of the elongated main body lead 101. In other embodiments of the present invention, purpose specific electrodes are used to facilitate the establishment of a low level electric field. Such purpose specific electrodes may be a metal tip and coil arrangement as depicted in FIG. 1, or may be linear strips such filar like strips, strands, threads or filaments that traverse all or part of the length of the elongated main body lead, windings, rings, plates, or the like. Electrodes may be made of a metal such as stainless steel, nitinol, or a conductive polymer such as, for example, polypyrrole. When energized, a low level electric field, preferably negative, emanates from the elongated main body lead 101 to repel platelets and reduce fibrosis and encapsulation. The structure may, in one embodiment of the present invention, continuously generate a low intensity electric field (up to 200 mV/cm, for example). In other embodiments, the electric field may be pulsed, sinusoidal, sporadic, or otherwise temporally patterned. The electric field may also, in some embodiments of the present invention, change polarity, gradient, strength, polarization, direction, or other parameters.

The inventors have discovered that implantable devices that continuously generate low intensity electric fields may be configured to reduce the incidence of acute vascular events and the progression of atherosclerotic disease. In particular, the inventors discovered that the risk for coronary ischemic events (e.g., recurrent myocardial infarction, recurrent angina, and the need for coronary revascularization) is attenuated among patients with an implantable cardioverter defibrillator (ICD).

In a non-limiting example, the electrode of an implantable cardioverter defibrillator (ICD) is implanted in the apex of the right ventricle, in close proximity to the coronary arterial system. The implantable cardioverter defibrillator (ICD) may be configured to continuously generate a low intensity electric field (up to 200 mV/cm, for example) that is compatible with beneficial endothelial effects on the coronary vasculature. In another example, an electrical field may be generated from an electrochemical gradient between a shocking coil and a metal tip of a lead. The different metals are affected by different pH values in the coil (blood flow) and tip (encapsulated in myocardial tissue) portions of the electrode. The electrochemical gradient may be adapted to generate a Sow intensity electric field.

Figure 2:
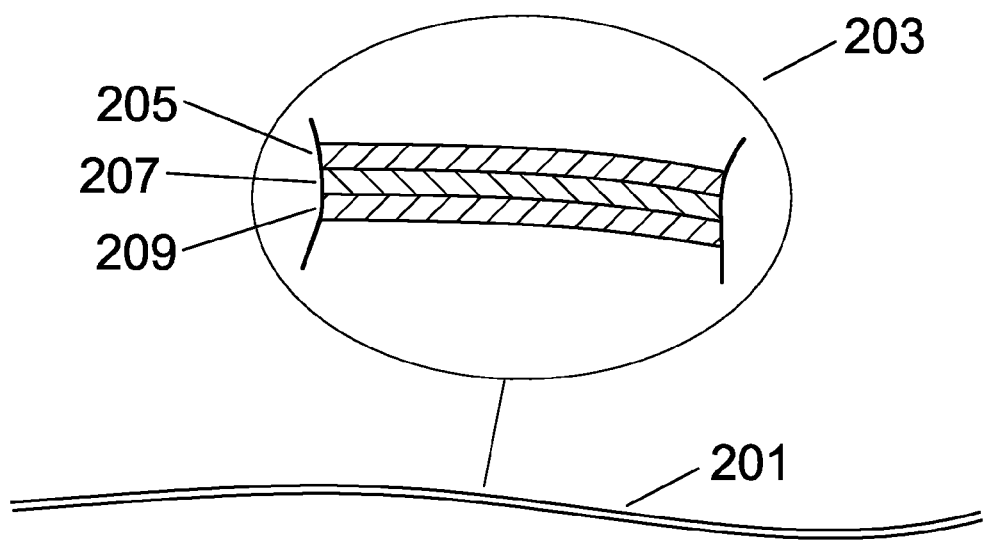
FIG. 2 depicts a lead having an electric field generating material.

FIG. 2 depicts a lead having an electric field generating material. The lead 201 may be implanted within a body either independently or in cooperation with other medical devices. One example is that of a cardiac rhythm management device where the lead of the device has a biocompatible coating such a polyurethane. An electric field generating material is placed either above or below the biocompatible coating, or the biocompatible coaling may be replaced with an electric field generating material. The electric field generating material may be the electric field source and may, in some embodiments of the present invention, further be an electrode or electrodes. Various electric field generating materials and dielectrics may be used to make the lead 201. A multi-layer structure 203 may make up the lead 201. A first lead layer 205, a second lead layer 207, and a third lead layer 209 are shown in FIG. 2. Other embodiments of the present invention may use more or fewer layers. An example of a multi-layer structure is the use of a piezoelectric material such as barium titanate, lead titanate, gallium orthophosphate, bismuth ferrite, sodium potassium niobate, sodium niobate, polyvinylidene fluoride, aluminum nitride, or the like. When using a piezoelectric material as a layer such as depicted by way of 207 in FIG. 2, layers containing conductive material such as gold, copper, platinum, molybdenum, and the like are further contained about the piezoelectric material, such as the first layer 205 and the third layer 209 depicted in FIG. 2. In such a topology, charge is created when the lead 201 deforms such that a force is created on the piezoelectric layer that in turn creates charge. The layers of piezoelectric material and conductive material may be deposited as a film or similar structure using techniques such as chemical vapor deposition, evaporation, or the like. In the ease of a piezoelectric material, internal pressure changes such as pressure changes due to blood flow and heart rhythms will cause a charge buildup in the piezoelectric structure and result in an electric field.

In another embodiment of the present invention, an electret material is used as a layer in the lead 201. The electric field layer 203 may contain one or more layers 205, 207 and 209. In one embodiment of the present invention, each of the layers comprises the same material. An electret material may be deposited or otherwise formed on or within the lead 201. An electret is a dielectric material that has an electric charge. An electret generates an electric field and may be used in conjunction with a metal layer or a polymer layer. There are two types of charges that create the electric field in an electret material. The first being polarization charges which are the result of the displacement of positive and negative charges within the material by way of preferential orientation caused by a strong electric field being applied while the material is in a liquid state during manufacture. The second source of charges being coulomb charges caused by an excess or deficiency of electrons over a portion of the material. These Coulomb charges generate longer range forces than polarization charges. It is also possible to generate regions of isolated charges at various locations in the material for therapeutic reasons that may be required with a given treatment regimen. Additives to the material may also improve coulomb charge storage in the material.

To form an electret layer, a suitable material is heated above its melting point in the presence of a strong electric field and then cooled in the presence of the strong electric field. Suitable materials include quartz, silicon dioxides, synthetic polymers such as fluoropolymers, polypropylene, polyethyleneterephthalate, polytetrafluoroethylene, parylene, and the like. Another way to create an electret layer in accordance with the present invention is to embed excess negative charge within a dielectric using a particle accelerator or depositing charges at or near the surface of a material using high voltage corona discharges. A process for making electrets is disclosed in U.S. Pat. No. 4,291,245 to Nowlin et al, and entitled "Electrets", the entire disclosure of which is incorporated herein by reference.

A process for making an anti-thrombotic coating for a medical device such as a stent, a vascular graft, a cardiac rhythm management device, a catheter, a vena cava filter, and the like, in one embodiment of the present invention involves converting an electret capable material into an electret either before coating a medical device, while coating a medical device, or after coating a medical device. The process comprises heating an electret capable material above its melting point to create a liquid, coating a medical device with the liquid, applying a strong electric field to the liquid, cooling the liquid to below it's melting point to create a solid coating, and removing the strong electric field. Another process technique to create an electric field generating coating on a medical device comprises forming an electret capable material into a medical device coating, applying a strong electric field to the medical device coating, increasing the Held strength of the electric field until corona discharge occurs, maintaining the corona discharge event for a dwell time, stopping the corona discharge event, and removing the electric field. In addition to an electric field generating coating, the medical device may also contain a component, such as insulation of a lead as in the device of FIG. 1, that produces a charge and an associated electric field.

Electroactive polymers may also be used to provide an electric field generating coating or structure for a medical device, and may be applied in conjunction with another material such as a piezoelectric material, electret material, or the like. Electroactive polymers may be dielectric or ionic, and may, in one embodiment of the present invention, be a ferroelectric polymer where they maintain a permanent electric polarization that may be reversed in the presence of an external electric field. One example of a ferroelectric polymer is polyvinylidene fluoride. Dielectric electroactive polymers include, for example, silicones and acrylic elastomers such as the acrylic elastomer VHB4910 available from the 3M Company, St. Paul, Minn. Examples of ionic electroactive polymers include conductive polymers and ionic polymer-metal composites.

Polyelectrolytes may also be used as an electric field generating material in accordance with the present invention. Polyelectrolytes are polymers whose repeating units have an electrolyte group. The polymers become charged when dissociated in water. For example, polyacrylic acid is negatively charged when dissociated in water, as is poly (sodium styrene sulfonate).

Galvani potential materials may further be used to provide an electric field generating coating or structure for a medical device in accordance with the present invention. Dissimilar metals may be joined together as a layer or composite structure. When two different metals make electrical contact, electrons flow from the metal with the lower work function to the metal with the higher work function, and an electric double layer is formed at the interface. In addition, semiconductor materials may be used and may, in some embodiments of the present invention, be combined with other materials such as electret materials, conductive materials, piezoelectric materials, and the like.

Figure 3:
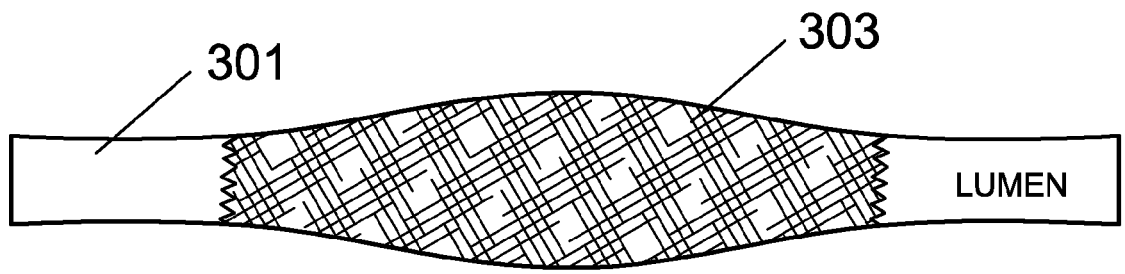
FIG. 3 illustrates a stent with electric field generating material.

In addition to a medical device such as that depicted by way of FIGS. 1 and 2, an electric field generating material will prove beneficial to other medical devices such as, for example, a stent. In-stent restenosis is a complication where there is a reclosure of a previously stenosed coronary artery. Atherosclerosis, a common disease of the arteries, occurs where fatty material accumulates on the smooth muscle of a vessel wall, resulting in the eventual impediment of blood flow. The use of an electric field generating material will reduce the occurrence of restenosis. FIG. 3 illustrates a stent with electric field generating material. A stent 303 may be coated or otherwise contain an electric field generating material. When deployed in a vessel 301, the electric field generating material serves to repel platelets and create an anti-thrombotic effect to reduce the likelihood of restenosis or similar vascular events that contribute to failure of the stented artery, clotting and associated complications, or the like.

Figure 4:
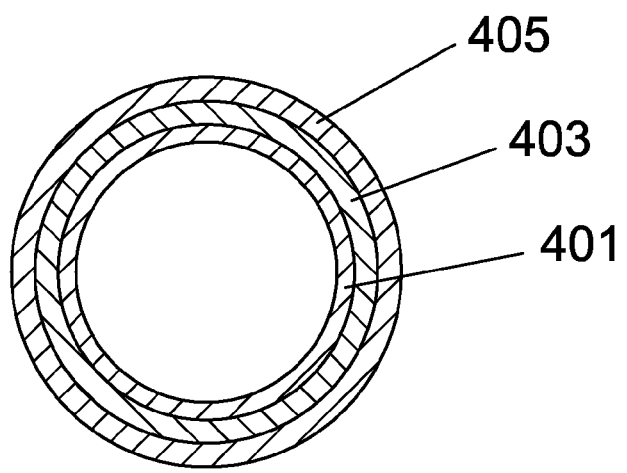
FIG. 4 is a cross sectional circumferential view of a stent with electric field generating material.
Figure 5:
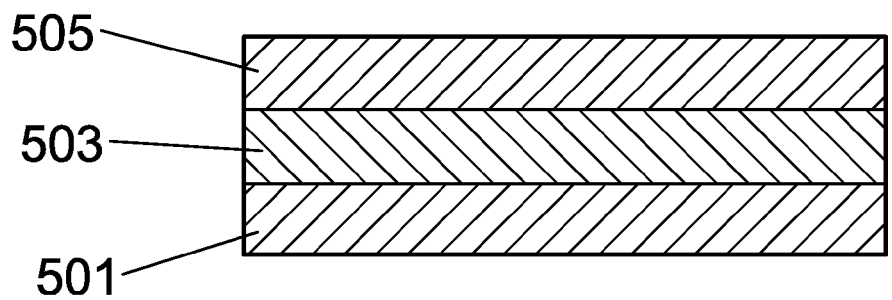
FIG. 5 is a cross sectional view of an electric field generating structure.

An electric field generating material may he disposed on the stent 303, such as a coating or covering, or the electric field generating material may be integral to the structure of the stent 303 and interspersed with the Interconnected elements that make up the mechanical structure of the stent. The mechanical structure of a stent is sometimes referred to as the scaffold. Various electric field generating materials and dielectrics may be used to provide the desired therapeutic effects in accordance with the present invention. FIG. 4 is a cross sectional circumferential view of a stent with electric field generating material showing a first circular layer 401, a second circular layer 403 and a third circular layer 405. Material layers may also be planar or otherwise compliant with the mechanical structure of a stent. FIG. 5 is a cross sectional view of an electric field generating structure as applied to a stent where a first stent layer 501, a second stent layer 503 and a third stent layer 505 can be seen. The various types of layers that may be used are further described herein. It should be noted that a single layer may be used (all layers are the same material, hence a single material layer). In other embodiments, more or fewer layers may be employed depending on the therapeutic objectives to be met. An example of a multi-layer structure is the use of a piezoelectric material such as barium titanate, lead titanate, gallium orthophosphate, bismuth ferrite, sodium potassium niobate, sodium niobate, polyvinylidene fluoride, aluminum nitride, or the like. When using a piezoelectric material as a layer such as depicted by way of 503 in FIG. 5 or 403 in FIG. 4, layers containing conductive material such as gold, copper, platinum, molybdenum, and the like are further contained about the piezoelectric material, such as the first stent layer 501 and the third stent layer 505 depicted in FIG. 5 or the first circular layer 401 and the third circular layer 405. In such a topology, charge is created when the material deforms such that a force is created on the piezoelectric layer that in turn creates charge. The layers of piezoelectric material and conductive material may be deposited as a film or similar structure using techniques such as chemical vapor deposition, evaporation, or the like. In the case of a piezoelectric material, internal pressure changes such as pressure changes due to blood flow and heart rhythms will cause a charge buildup in the piezoelectric structure and result in an electric field.

Figure 6:
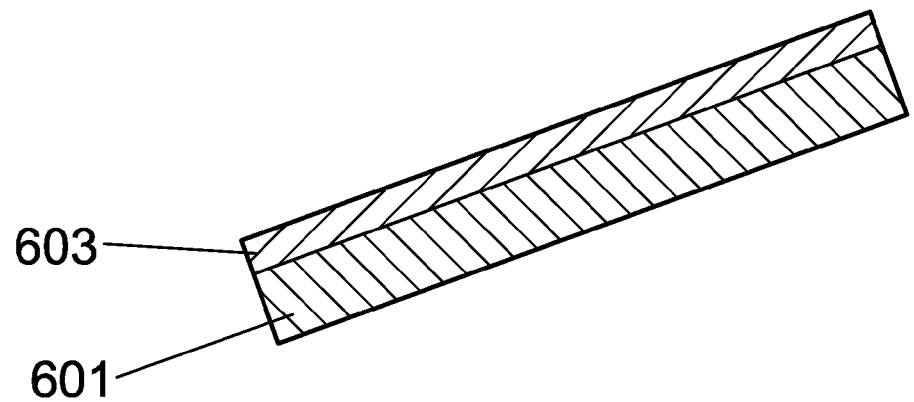
FIG. 6 is a cross sectional view of another electric field generating structure.

In another embodiment of the present invention, an electret material is used as a layer. The electric field material may contain one or more layers 401, 403 and 405 as shown in FIG. 4, or one or more layers 501, 503 and 505 as shown in FIG. 5. FIG. 6 further depicts a two layer approach with a first planar layer 601 and a second planar layer 603. More or less layers may also be employed. In one embodiment of the present invention, each of the layers comprises the same material. An electret material may be deposited, disposed on, or otherwise interspersed within or upon a stent. An electret is a dielectric material that has an electric charge. An electret generates an electric field and may be used in conjunction with a metal layer or a polymer layer. There are two types of charges that create the electric field in an electret material. The first being polarization charges which are the result of the displacement of positive and negative charges within the material by way of preferential orientation caused by a strong electric field being applied while the material is in a liquid state during manufacture. The second source of charges being coulomb charges caused by an excess or deficiency of electrons over a portion of the material. These coulomb charges generate longer range forces than polarization charges. It is also possible to generate regions of isolated charges at various locations in the material for therapeutic reasons that may be required with a given treatment regimen. Additives to the material may also improve coulomb charge storage in the material.

To form an electret layer, a suitable material is heated above its melting point in the presence of a strong electric field and then cooled in the presence of the strong electric field. Suitable materials include quartz, silicon dioxides, synthetic polymers such as fluoropolymers, polypropylene, polyethyleneterephthalate, polytetrafluoroethylene, parylene, and the like. Another way to create an electret layer in accordance with the present invention is to embed excess negative charge within a dielectric using a particle accelerator or depositing charges at or near the surface of a material using high voltage corona discharges. A process for making electrets Is disclosed in U.S. Pat. No. 4,291,245 to Nowlin et al, and entitled "Electrets", the entire disclosure of which is incorporated herein by reference.

A process for making an antithrombotic coating for a medical device such as a stent, a vascular graft, a cardiac rhythm management device, a catheter, a vena cava filter, and the like, in one embodiment of the present invention involves converting an electret capable material into an electret either before coating a medical device, while coating a medical device, or after coating a medical device. The process comprises heating an electret capable material above its melting point to create a liquid, coating a medical device with the liquid, applying a strong electric field to the liquid, cooling the liquid to below it's melting point to create a solid coating, and removing the strong electric field. Another process technique to create an electric field generating coating on a medical device comprises forming an electret capable material into a medical device coating, applying a strong electric field to the medical device coating, increasing the field strength of the electric field until corona discharge occurs, maintaining the corona discharge event for a dwell time, stopping the corona discharge event, and removing the electric field. In addition to an electric field generating coaling, the medical device may also contain a component, such as insulation of a lead as in the device of FIG. 1, that produces a charge and an associated electric field.

Electroactive polymers may also be used to provide an electric field generating coating or structure for a stent, and may be applied in conjunction with another material such as a piezoelectric material, electret material, or the like. Electroactive polymers may be dielectric or ionic, and may, in one embodiment of the present invention, be a ferroelectric polymer where they maintain a permanent electric polarization that may be reversed in the presence of an external electric field. One example of a ferroelectric polymer is polyvinylidene fluoride. Dielectric electroactive polymers include, for example, silicones and acrylic elastomers such as the acrylic elastomer VHB4910 available from the 3M Company, St. Paul, Minn. Examples of ionic electroactive polymers include conductive polymers and ionic polymer-metal composites.

Polyelectrolytes may also be used as an electric field generating material in accordance with the present invention. Polyelectrolytes are polymers whose repeating units have an electrolyte group. The polymers become charged when dissociated in water. For example, polyacrylic acid is negatively charged when dissociated in water, as is poly (sodium styrene sulfonate).

Galvani potential materials may further be used to provide an electric field generating coating or structure for a stent in accordance with the present invention. For example, a metal portion of the stent may be embedded in the endothelial wall of the blood vessel and another metal portion of the stent may be exposed to blood flow in the lumen. The two metal portions may be adapted to generate a low intensity electrical field between them through, for example, a difference in pH between the two metal portions. Dissimilar metals may be joined together as a layer or composite structure or further be used as part of the mechanical structure of the stent itself, for example, as part of the scaffold. When two different metals make electrical contact, electrons flow from the metal with the lower work function to the metal with the higher work function, and an electric double layer is formed at the interface. In addition, semiconductor materials may be used and may, in some embodiments of the present invention, be combined with other materials such as electret materials, conductive materials, piezoelectric materials, and the like. The ranges of the electrical field associated with this device and the various embodiments described herein include the coronary system, with more focused energy applied in the implanted area where more severe coronary artery disease exists.

Figure 7:
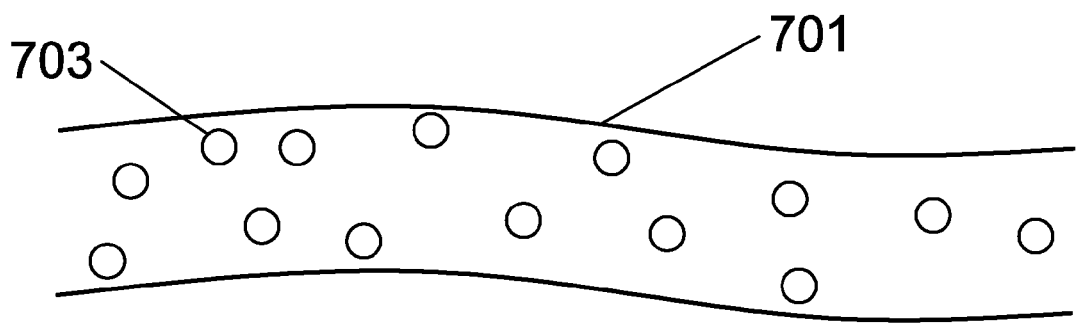
FIG. 7 depicts a vessel with electric field point sources.

Turning now to FIG. 7, a vessel with electric field point sources is depicted. The various electric field generating materials heretofore described may also be used to lubricate an electric field point source 703 that creates a localized electric field for therapeutic and preventative purposes. The electric field point source 703 may comprise a bead, a plate, a grommet, a strand, a fiber, a sphere, or the like. The electric field point source 703 is fastened or otherwise placed in proximity to a vessel 701. Fastening and placement may be performed through a variety of techniques such as sutures, biocompatible adhesives, implantation, and the like.

Figure 8:
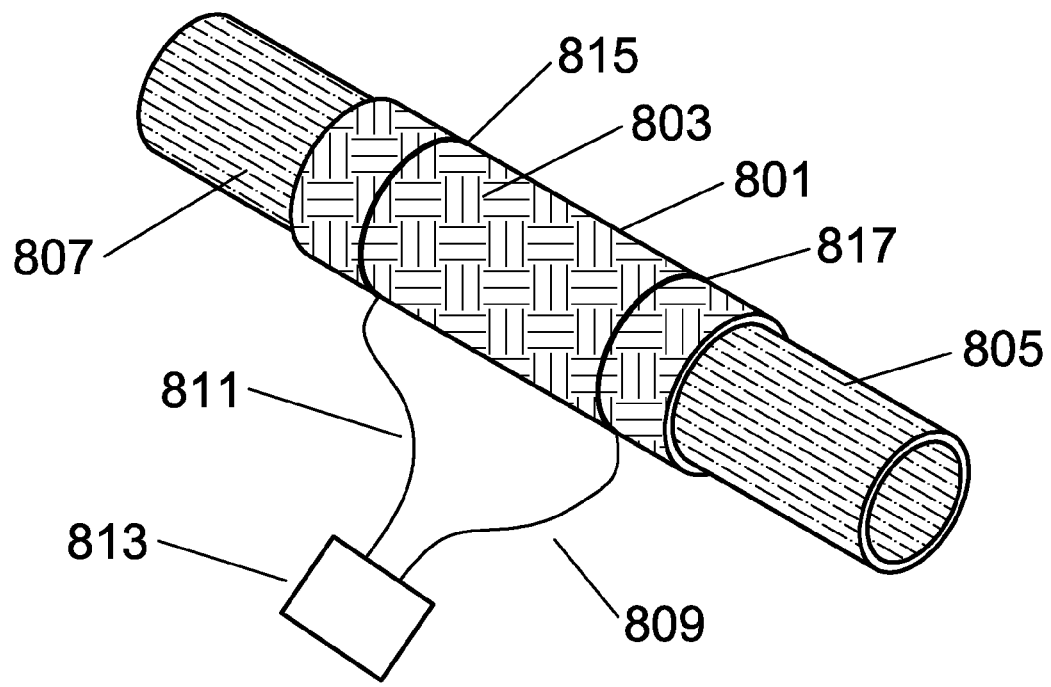
FIG. 8 depicts a vascular graft with an electric field source.

FIG. 8 depicts a vascular graft with an electric field source 801. Shown is a vessel first section 805 and a vessel second section 807. The vascular graft 801 contains or is made from an electric field generating material and may contain a dielectric composite 803 for the purpose of providing a charge and associated electric field to the vascular graft 801 the purpose of healing as well as the reduction of graft failure and related events. A first electrode source 815 and a second electrode source 817 are depicted, and may be made from a biocompatible metal or conductive polymer. The first electrode source 815 and the second electrode source 817 may further be a ring, a plate, a strand or fiber, a cylinder, or the like. The first electrode source 815 and the second electrode source 817 are electrically connected to a power source 813 by way of a first conductive lead 809 and a second conductive lead 811. The vascular graft 801 is implanted and the electric field provides therapeutic and preventive effects.

Figure 9:
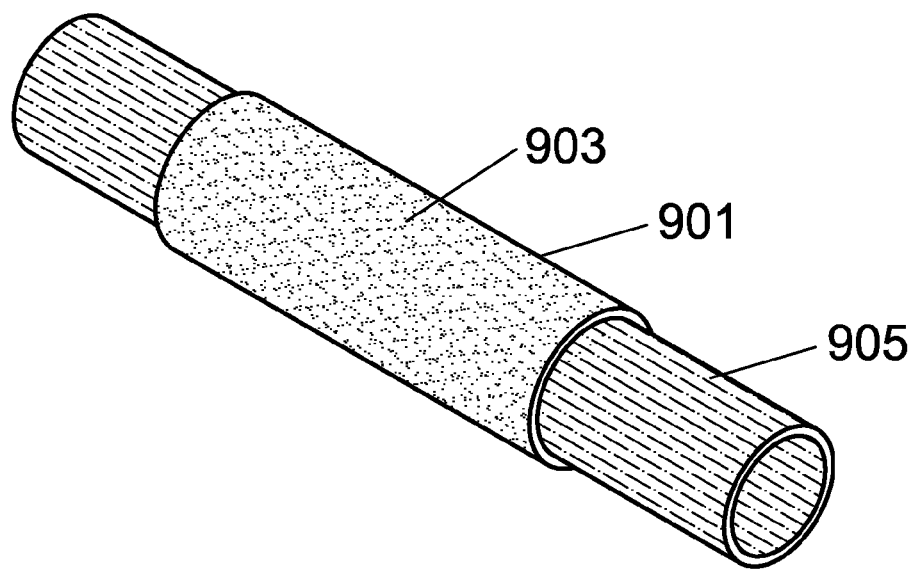
FIG. 9 depicts a vascular graft with electric field generating material.

Another embodiment of the present invention is a vascular graft with electric field generating material, as depicted in FIG. 9. A vascular graft 901 comprising electric field material 905 is depicted surrounding or otherwise replacing a diseased or damaged vessel 905.

A vascular graft may be coated or otherwise contain an electric field generating material. When implanted, the electric field generating material serves to repel platelets and create an antithrombotic effect to reduce the likelihood of blockage or similar vascular events that contribute to failure of the graft, clotting and associated complications, or the like.

An electric field generating material may be disposed on the vascular graft, such as by way of a coating or covering, or the electric field generating material may be integral to the structure of the vascular graft and interspersed with the mechanical structure of the graft Various electric field generating materials and dielectrics may be used to provide the desired therapeutic effects in accordance with the present invention. Multiple or single layers may be applied to the vascular graft, or the selected materials woven or otherwise integrated to the vascular graft structure. An example of a multi-layer structure is the use of a piezoelectric material such as barium titanate, lead titanate, gallium orthophosphate, bismuth ferrite, sodium potassium niobate, sodium niobate, polyvinylidene fluoride, aluminum nitride, or the like. When using a piezoelectric material as a layer, layers containing conductive material such as gold, copper, platinum, molybdenum, and the like are further contained about the piezoelectric material. In such a topology, charge is created when the material deforms such that a force is created on the piezoelectric layer that in turn creates charge. The layers of piezoelectric material and conductive material may be deposited as a film or similar structure using techniques such as chemical vapor deposition, evaporation, or the like. In the case of a piezoelectric material, internal pressure changes such as pressure changes due to blood flow and heart rhythms will cause a charge buildup in the piezoelectric structure and result in an electric field.

In another embodiment of the present invention, an electret material is used as a layer or a fiber within the vascular graft. The electric field material may contain one or more layers. In one embodiment of the present invention, each of the layers comprises the same material. An electret material may be deposited, disposed on, or otherwise interspersed within or upon the vascular graft. An electret is a dielectric material that has an electric charge. An electret generates an electric field and may be used. In conjunction with a metal layer or a polymer layer. There are two types of charges that create the electric field in an electret material. The first being polarization charges which are the result of the displacement of positive and negative charges within the material by way of preferential orientation caused by a strong electric field being applied while the material is in a liquid state during manufacture. The second source of charges being coulomb charges caused by an excess or deficiency of electrons over a portion of the material. These coulomb charges generate longer range forces than polarization charges. It is also possible to generate regions of isolated charges at various locations in the material for therapeutic reasons that may be required with a given treatment regimen. Additives to the material may also improve coulomb charge storage in the material.

To form an electret layer, a suitable material is heated above its melting point in the presence of a strong electric field and then cooled in the presence of the strong electric field. Suitable materials include quartz, silicon dioxides, synthetic polymers such as fluoropolymers, polypropylene, polyethyleneterephthalate, polytetrafluoroethylene, parylene, and the like. Another way to create an electret layer in accordance with the present invention is to embed excess negative charge within a dielectric using a particle accelerator or depositing charges at or near the surface of a material using high voltage corona discharges. A process for making electrets is disclosed in U.S. Pat. No. 4,291,245 to Nowlin et al, and entitled "Electrets", the entire disclosure of which is incorporated herein by reference.

A process for making an electric field generating material for a medical device such as a stent, a vascular graft, a cardiac rhythm management device, a catheter, a vena cava filter, and the like, in one embodiment of the present invention involves converting an electret capable material into an electret either before coating a medical device, while coating a medical device, or after coating a medical device. The process comprises heating an electret capable material above its melting point to create a liquid, coating a medical device with the liquid, applying a strong electric field to the liquid, cooling the liquid to below it's melting point to create a solid coaling, and removing the strong electric field. Another process technique to create an electric field generating coating on a medical device comprises forming an electret capable material into a medical device coating, applying a strong electric field to the medical device coating, increasing the field strength of the electric field until corona discharge occurs, maintaining the corona discharge event for a dwell time, stopping the corona discharge event, and removing the electric field. In addition to an electric field generating coating, the medical device may also contain a component, such as a fiber or composite structure that produces a charge and an associated electric field.

Electroactive polymers may also be used to provide an electric field generating coating or structure for a vascular graft, and may be applied in conjunction with another material such as a piezoelectric material, electret material, or the like. Electroactive polymers may be dielectric or ionic, and may, in one embodiment of the present invention, be a ferroelectric polymer where they maintain a permanent electric polarization that may be reversed in the presence of an external electric field. One example of a ferroelectric polymer is polyvinylidene fluoride. Dielectric electroactive polymers include, for example, silicones and acrylic elastomers such as the acrylic elastomer VHB4910 available from the 3M Company, St Paul, Minn. Examples of ionic electroactive polymers include conductive polymers and ionic polymer-metal composites.

Polyelectrolytes may also be used as an electric field generating material in accordance with the present invention. Polyelectrolytes are polymers whose repeating units have an electrolyte group. The polymers become charged when dissociated in water. For example, polyacrylic acid is negatively charged when dissociated in water, as is poly(sodium styrene sulfonate).

Galvani potential materials may further be used to provide an electric field generating coating or structure for a vascular graft in accordance with the present invention. Dissimilar metals may be joined together as a layer or composite structure or further be used as part of the mechanical structure of the vascular graft itself. When two different metals make electrical contact, electrons flow from the metal with the lower work function to the metal with the higher work function, and an electric double layer is formed at the interface. In addition, semiconductor materials may be used and may, in some embodiments of the present invention, be combined with other materials such as electret materials, conductive materials, piezoelectric materials, and the like.

In another embodiment of the present invention, electret fibers are woven or otherwise integrated into the vascular graft 901. Electret fibers may be, for example polypropylene fibers, polyethylene terephthalate fibers. As the fibers are made, a strong electric field is applied to convert the fibers into electret fibers. There are two types of charges that create the electric field in an electret material. The first being polarization charges which are the result of the displacement of positive and negative charges within the material by way of preferential orientation as a strong electric field is applied while the material is liquid. The second being coulomb charges caused by an excess or deficiency of electrons over a portion of the material. These coulomb charges generate longer range forces than polarization charges. It is also possible to generate regions of isolated charges at various locations in the material for various therapeutic reasons. Additives to the material may also improve coulomb charge storage in the material.

Triboelectric charging generates free charges on the material, and results whenever two dissimilar materials are brought into contact and then separated. In order for the two dissimilar materials to produce useful electric fields, it is important that at least one of the materials be a sufficiently good insulator to maintain its charged state for the required period of time.

Various embodiments of the present invention may locate charged zones or regions on or within the vascular graft for specific therapeutic effects. For example, a prosthetic arterial graft when first implanted requires proper healing at each end where the prosthetic structure meets the original artery. Therefore, a compliment of positive charge zones along a periphery surface of the prosthetic graft may in tact promote healing and proper bonding, whereas a negatively charged zone may prevent unwanted fibrosis and scarring. In addition, the materials selected for electric field generation may also have a specific lifetime of charge. For example, after a specified period of healing has elapsed, the positive charge periphery or zone may then become charge neutral, or may invert and become charge negative. Charge zones may also promote improved hemodynamic response and biological reactivity. Further, proper placement of charge zones in a vascular graft or other medical device may create a biomimetic zone within the graft, or a zone that promotes tissue growth in a given direction. Such directional tissue growth could be valuable in replacement surgery where damaged tissue is replaced with an engineered material that requires tissue integration and growth in certain zones and no growth in other zones of the device. Tissue engineering using charged materials of the present invention may be applied to stents, vascular grafts, cardiac rhythm management devices, catheters, vena cava filters, and the like.

Figure 10:
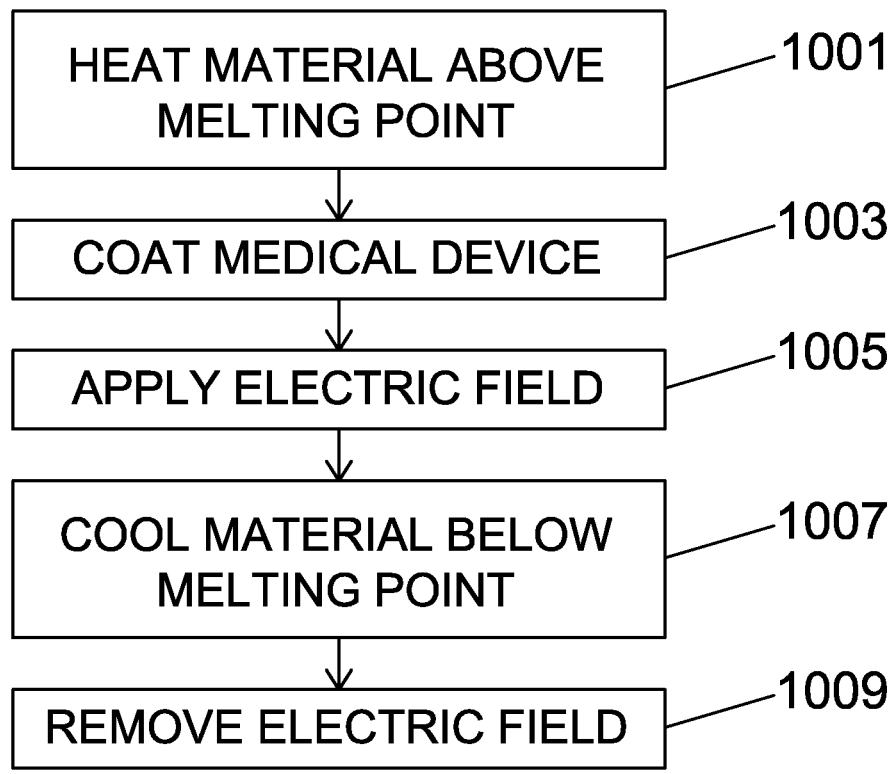
FIG. 10 is a process flow diagram that depicts the steps for making a coating for a medical device.
Figure 11:
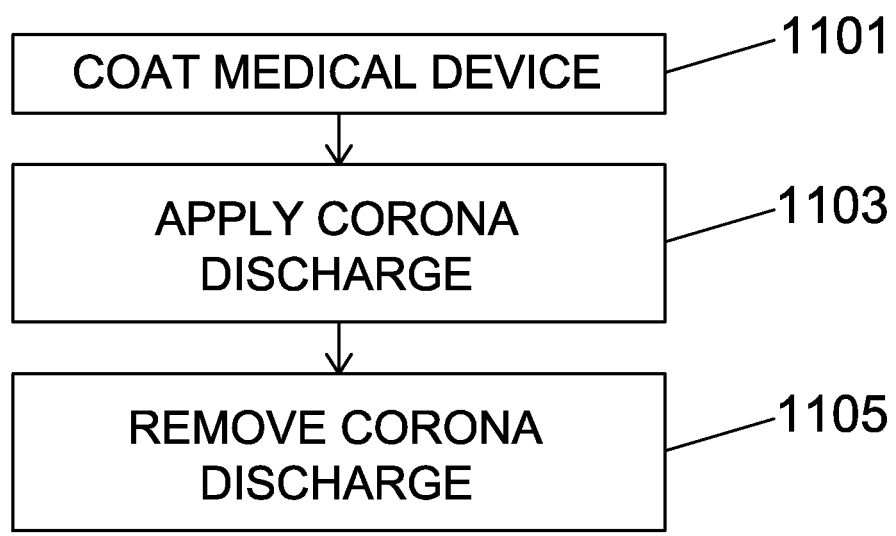
FIG. 11 is an alternative process flow diagram that depicts the steps for making a coaling for a medical device.

Various techniques may be used to apply an electric field generating material to a medical device. The electric field generating material may be applied as a coating, a component, a layer, an integral structural component, and the like. When making an electret material, for example, there are several techniques that can be used. FIGS. 10 and 11 are exemplary process flow diagrams depicting a method for making an antithrombotic coating for a medical device where the coating is an electret that creates an electric field. In FIG. 10, an electret capable material is heated above its melting point in step 1001. A medical device is then coated with the liquid material in step 1003 and a strong electric field is applied in step 1005. The liquid material is then cooled to below its melting point in step 1007 and the electric field is removed in step 1009. Variations of this basic process may be carried out that are dependent on the medical device, desired therapeutic effect, and the like. For example, if the medical device contains sensitive electronic components, the electret formation steps (step 1005 where a strong electric field is applied) may take place where the coating or other structure is not In contact with or in proximity to the medical device containing sensitive electronic components. Or, in an alternative process, the electronics are Installed in the medical device after the heretofore described process takes place. Another exemplary process for creating an electric field generating coating for a medical device is depicted in FIG. 11. In step 1101, an electret capable material is formed into a coating for a medical device. In step 1103 a strong electric field is applied to the medical device coating to the point of corona discharge. The corona discharge event is maintained for a specified dwell time, that dwell time being dependent on process variables such as the electret capable material chosen, the required charge density, and the like. In step 1105, the corona discharge is removed by reducing and then eliminating the applied strong electric field. FIGS. 10 and 11 are intended to be examples, and not limitations, of processes mat may be used to make the present invention and the various embodiments described herein.

The various embodiments described herein may be applied to the treatment of various diseases, including cardiovascular disease, peripheral vascular disease, or any disease process in which induction of angiogenesis can lead to an improved outcome.

The following description addresses the treatment of coronary artery disease, which is but one of the many diseases treatable using the devices and methods described herein. For the treatment of coronary artery disease, a device of the present invention may be implanted in one of the following locations: right ventricular apex (similar to the current location of ICD leads), intracoronary (similar to the current location of coronary stents); coronary sinus or cardiac vein (similar to the current location of biventricular devices). For this application, which is a chronic and progressive disease process, the implanted device in it's active embodiment state (powered by a battery or capacitor), the device may be adapted to generate a continuous low intensity electric field in the range of 100-300 mV/cm for an extended period of time (e.g., a period of years). The ranges of the electrical field may be limited to a specific diseased area (e.g., 1-2 cm) or to encompass additional parts of the coronary system (5-10 cm).

The devices of the present invention are also suitable for the treatment of acute athero-thrombotic events, such as acute myocardial infarction, stroke, and acute renal or peripheral arterial occlusion. For an acute athero-thrombotic event, the devices of the present invention may be used to accelerate the healing process of an ischemic organ. The devices of the present invention are also effective for limiting the amount of tissue necrosis and/or infarction following an acute ischemic event. Early tissue reflow may be accomplished by employing low intensity electric fields that are adapted to improve endothelial function and to enhance microvascular flow through angiogenesis following tissue ischemia.

For the treatment of acute athero-thrombotic events, the implantable device may be applied for a limited period of time (e.g., a week to a few months) until the process of tissue healing is complete. Currently, CCDs are typically implanted and remain active for an extended period of time (e.g., a number of years), so it may be useful to implant the devices of the invention to prevent the progression of atherosclerotic disease indefinitely. In some cases, however, where a limited treatment is warranted, the devices may be removed or may remain inactive for future applications (e.g., a recurrent coronary event).

The present invention is also useful for the prevention of thromboembolic events in high risk patients with atrial fibrillation. Low intensity electric fields may be used to stabilize the atrial endomyocardial and to prevent clot formation in high risk patients with atrial fibrillation. For this disease, it may be preferable to implant the device of the first embodiment in a fashion similar to currently used atrial pacemaker leads. The device may be adapted to generate a continuous electric field for an extended period of time or can be removed when atrial fibrillation is fully controlled and the risk for arterial thromboembolic events is reduced.

Although the embodiments described herein have referenced continuous electric fields, intermittent electrical fields are also within the scope of the present invention.

The present Invention is also useful for the treatment and prevention of the progression of arterial (noncardiac) vascular disease. For example, an implanted device may t delay the progression of atherosclerotic disease through continuous generation of electric fields that are adapted to improve endothelial function and to enhance angiogenesis in patients with appropriate risk levels. All of the devices described herein are suitable for application in various locations (including, but not limited to, peripheral arteries, renal arteries, carotid/cerebral arteries, and the aorta). The devices described herein may also be useful for inhibiting the development or progression of Alzheimer's disease due to cerebral vasculopathy. For these types of chronic conditions, the devices described herein may be applied for an extended period of time, such as a period of years.

Additionally, the present invention is useful for the prevention of restenosis following revascularization procedures. Current revascularization procedures are limited by a relatively high rate of restenosis and acute thrombosis following stent implantation. An Implantable device that favorably affects the endothelium as described above may be adapted to reduce the risk of restenosis and acute thrombotic events following revascularization procedures. The devices described herein may also be used for the prevention of vein graft stenosis following coronary artery bypass grafting (CABG).

The devices described herein are also useful for the treatment of any condition that would benefit from exposure to a low intensity electrical stimulation as described herein. The stimulation may be placed in proximity to the target area, such as a coronary artery or bypass graft.

Numerous modifications and variations of the present Invention are possible In light of the above teachings. It is therefore to be understood that within the scope of the appended claims, the invention may be practiced otherwise than as specifically described herein.

It is, therefore, apparent that there has been provided, in accordance with the various t objects of the present invention, an implantable device that generates low intensity electric fields for the treatment of atherosclerotic disease and prevention of ischemic vascular events and methods of manufacturing such devices.

While the various objects of this invention have been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of this specification, drawings, and the claims appended herein.

What is claimed is:

1. An implantable medical device comprising:
   a discrete electric field point source with an instrinsic electric charge and adapted for fastening and placement to a vessel of a living organism, the discrete electric field point source comprising an electric field generating material capable of generating a localized electric field in proximity to the discrete electric field point source without connection to a power supply; wherein the discrete electric field point source is substantially smaller than the implantable medical device.

2. The internal medical device of claim 1, wherein said electric field generating material of the electric field point source is selected from the group consisting of an electret material, an electroactive polymer material, a polyether material, a polyelectrolyte, and a galvani potential material.

3. A stent for transluminal implantation comprising a first end and a second end; interconnected elements forming a generally elongated tubular form; and a discrete electric field point source with an intrinsic electric charge and adapted for fastening and placement to a vessel of a living organism, the discrete electric field point source comprising an electric field generating material capable of generating a localized electric field in proximity to the discrete electric field point source without connection to a power supply; wherein the discrete electric field point source is substantially smaller than the stent.

4. The stent of claim 3, wherein said electric field generating material of the electric field point source is selected from the group consisting of an electret material, an electroactive polymer material, a polyether material, a polyelectrolyte, and a galvani potential material.

5. A vascular graft having a first end and a second end and a wall with an inner and an outer surface longitudinally extending between the ends; a discrete electric field point source with an intrinsic electric charge and adapted for fastening and placement to a vessel of a living organism, the discrete electric field point source comprising an electric field generating material capable of generating a localized electric field in proximity to the discrete electric field point source without connection to a power supply; wherein the discrete electric field point source is substantially smaller than the vascular graft.

6. The vascular graft of claim 5, wherein said electric field generating material of the electric field point source is selected from the group consisting of an electret material, an electroactive polymer material, a polyether material, a polyelectrolyte, and a galvani potential material.

7. The vascular graft of claim 5 further comprising a transluminal electrode.

\* \* \* \* \*

UNITED STATES PATENT AND TRADEMARK OFFICE
CERTIFICATE OF CORRECTION

PATENT NO. : 9,492,652 B2  
APPLICATION NO. : 13/581313  
DATED : November 15, 2016  
INVENTOR(S) : Arthur Jay Moss et al.

Page 1 of 1

It is certified that error appears in the above-identified patent and that said Letters Patent is hereby corrected as shown below:

In the Claims

Column 14, Line 33, Claim 2, 'The internal medical device of claim 1' should read -The implantable medical device of claim 1-

Signed and Sealed this  
Twenty-fourth Day of October, 2017

Joseph Matal  
*Performing the Functions and Duties of the*  
*Under Secretary of Commerce for Intellectual Property and*  
*Director of the United States Patent and Trademark Office*